US007696384B2

(12) United States Patent
Cauwenberge et al.

(10) Patent No.: US 7,696,384 B2
(45) Date of Patent: *Apr. 13, 2010

(54) PROCESS FOR PRODUCING ETHYLENEAMINES

(75) Inventors: Gunther Van Cauwenberge, Temse (BE); Johann-Peter Melder, Boehl-Iggelheim (DE); Holger Evers, Munich (DE); Till Gerlach, Ludwigshafen (DE); Frank Kiesslich, Dietzenbach (DE); Ekkehard Schwab, Neustadt (DE); Bram Willem Hoffer, Heidelberg (DE)

(73) Assignee: BASF SE, Ludwigshafen (DE)

( * ) Notice: Subject to any disclaimer, the term of this patent is extended or adjusted under 35 U.S.C. 154(b) by 52 days.

This patent is subject to a terminal disclaimer.

(21) Appl. No.: 12/088,715

(22) PCT Filed: Sep. 25, 2006

(86) PCT No.: PCT/EP2006/066667

§ 371 (c)(1),
(2), (4) Date: Mar. 31, 2008

(87) PCT Pub. No.: WO2007/036498

PCT Pub. Date: Apr. 5, 2007

(65) Prior Publication Data

US 2008/0255360 A1  Oct. 16, 2008

(30) Foreign Application Priority Data

Sep. 30, 2005 (DE) .................. 10 2005 047 464
Feb. 6, 2006 (EP) ......................... 06101332

(51) Int. Cl.
*C07C 211/00* (2006.01)
(52) U.S. Cl. ..................................... 564/463
(58) Field of Classification Search ............ None
See application file for complete search history.

(56) References Cited

U.S. PATENT DOCUMENTS

| | | | |
|---|---|---|---|
| 4,014,933 A | 3/1977 | Boettger et al. | |
| 4,568,746 A | 2/1986 | Cowherd, III | |
| 4,647,663 A | 3/1987 | Dixon et al. | |
| 4,855,505 A | 8/1989 | Koll | |
| 5,002,922 A | 3/1991 | Irgang et al. | |
| 5,410,086 A | 4/1995 | Burgess | |
| 5,958,825 A | 9/1999 | Wulff-Döring et al. | |
| 6,187,957 B1 | 2/2001 | Meyer et al. | |
| 6,525,222 B2 | 2/2003 | Nouwen et al. | |
| 7,393,978 B2 | 7/2008 | Frauenkron et al. | |
| 2005/0107637 A1 | 5/2005 | Gerlach et al. | |
| 2007/0043217 A1 | 2/2007 | Siegert et al. | |
| 2007/0100144 A1 | 5/2007 | Frauenkron et al. | |
| 2008/0221359 A1 | 9/2008 | Gerlach et al. | |
| 2008/0255351 A1 | 10/2008 | Hoffer et al. | |
| 2009/0030237 A1 | 1/2009 | van Cauwenberge et al. | |

FOREIGN PATENT DOCUMENTS

| | | |
|---|---|---|
| DE | 1953263 | 2/1972 |
| DE | 19859776 | 6/2000 |
| DE | 10349059 | 5/2005 |
| EP | 0036331 | 9/1981 |
| EP | 0382049 | 8/1990 |
| EP | 0839575 | 5/1998 |
| EP | 0963975 | 12/1999 |
| EP | 1106600 | 6/2001 |
| GB | 1508460 | 4/1978 |
| JP | 59115746 | 7/1984 |
| WO | WO-96/38226 | 12/1996 |
| WO | WO-03/010125 | 2/2003 |
| WO | WO-03/076386 | 9/2003 |
| WO | WO-2005/012223 | 2/2005 |
| WO | WO-2005/014523 | 2/2005 |
| WO | WO-2005/061430 | 7/2005 |
| WO | WO-2006/114417 | 11/2006 |

(Continued)

OTHER PUBLICATIONS

Arné, M., "Alkyl Amines", SRI International, 1981, Report No. 138, pp. 7,8,13-16, 43-107, 113 & 117.

(Continued)

*Primary Examiner*—Brian J Davis
(74) *Attorney, Agent, or Firm*—Connolly Bove Lodge & Hutz LLP

(57) ABSTRACT

Processes comprising: providing a starting material comprising monoethanolamine; and reacting the starting material with ammonia in the presence of a heterogeneous transition metal catalyst to form a reaction product comprising one or more ethylene amines; wherein the catalyst comprises a catalytically active composition, which prior to treatment with hydrogen, comprises a mixture of oxygen-containing compounds of aluminum, copper, nickel and cobalt; and wherein the catalyst is present as one or more shaped catalyst particles selected from spheres, extrudates, pellets and other geometries, wherein the sphere or extrudate has a diameter of <3 mm, the pellet has a height of <3 mm, and the other geometries have an equivalent diameter $L=1/a'$ of <0.70 mm, where $a'$ is the external surface area per unit volume $(mm_s^2/mm_p^3)$, as defined by $$a' = \frac{A_p}{V_p}$$

where $A_p$ is the external surface area of the catalyst particle $(mm_s^2)$ and $V_p$ is the volume of the catalyst particle $(mm_p^3)$.

19 Claims, No Drawings

FOREIGN PATENT DOCUMENTS

| WO | WO-2007/036496 | 4/2007 |
| --- | --- | --- |
| WO | WO-2007/036499 | 4/2007 |
| WO | WO-2007/093514 | 8/2007 |

OTHER PUBLICATIONS

Barnes, C. M., et al., "Ethylenediamine by Low-Pressure Ammonolysis of Monoethanolamine", Ind. Eng. Chem. Prod. Res. Dev., 1981, vol. 20, pp. 399-407.

Catalysis in Kirk Othmer Encyclopedia of Chemical Technology Copyright © 2002 by John Wiley & Sons, Inc. pp. 200-254.

Kronich, I. G., et al., "Gas-Phase Synthesis of Morpholine from Diethylene Glycol and Ammonia", The Soviet Chemical Industry, 1982, vol. 14, No. 11, pp. 1318-1330.

Khim, Prom-st. (Moscow), 1982, vol. 11, pp. 653-655.

Zh. Vses. Khim. Obshchest., 1969, vol. 14, No. 5, pp. 589-590.

Kusaka, H., et al., "Characterization and Nitrite Group Hydrogenation Study of Supported and Unsupported Ru-Co Catalyst", Journal of Catalysis, 1996, vol. 161, pp. 96-106.

US 7,696,384 B2

PROCESS FOR PRODUCING ETHYLENEAMINES

CROSS-REFERENCE TO RELATED APPLICATIONS

This application is a national stage application, under 35 U.S.C. §371, of PCT/EP2006/066667, filed Sep. 25, 2006, which claims priority of German Patent Application No. 102005047464.0, filed Sep. 30, 2005 and European Patent Application No. 06101332.2, filed Feb. 6, 2006.

BACKGROUND OF THE INVENTION

Ethylene amines are used, inter alia, as solvents, stabilizers, for the synthesis of chelating agents, synthetic resins, drugs, inhibitors and surface-active substances.

Diethylenetriamine(bis(2-aminoethyl)amine; DETA), in particular, is used as solvent for dyes and is a starting material for the production of ion exchangers, pesticides, antioxidants, corrosion inhibitors, complexing agents, textile assistants and absorbents for (acidic) gases.

Numerous processes for preparing ethylene amines are described in the literature.

According to PEP Report No. 138, "Alkyl Amines", SRI International, 03/1981, in particular pages 7, 8, 13-16, 43-107, 113, 117, the reaction of dichloroethane with ammonia at a molar ratio of 1:15 gives diethylenetriamine (DETA) in a proportion of greater than 20% by weight based on the ethylene amines formed. However, 40% by weight of higher ethylene amines are formed in addition to 40% by weight of ethylenediamine (EDA).

The formation of these higher ethylene amines (i.e. ethylene amines having a boiling point above that of triethylenetetramine (TETA)) can be substantially suppressed in favor of ethylene diamine by amination of monoethanolamine (MEOA) with ammonia (cf., for example, the abovementioned PEP Report, U.S. Pat. No. 4,014,933 (BASF AG)). However, aminoethylethanolamine (AEEA) and piperazine (PIP) are formed as by-products in this reaction.

Ind. Eng. Chem. Prod. Res. Dev. 1981, 20, pages 399-407, (C. M. Barnes et al.) describes the ammonolysis of MEOA to EDA over nickel catalysts on a mixed $SiO_2$—$Al_2O_3$ support. Addition of water and the powdered catalyst is said to be advantageous in increasing the yield of EDA.

Disadvantages of these technologies involving suspension catalysis result, inter alia, from the need to separate the catalyst from the product. In addition, the selectivities, e.g. for the formation of DETA, are in need of improvement.

WO-A-05/014523 (BASF AG) relates to a process for preparing ethylene amines (e.g. DETA) by reaction of monoethanolamine (MEOA) with ammonia in the presence of a catalyst in a reactor (1) and fractionation of the resulting reaction product mixture, with ethylenediamine (EDA) obtained in the fractionation being reacted in a separate reactor (2) in the presence of a catalyst to form diethylenetriamine (DETA) and the resulting reaction product mixture being fed to the fractionation of the reaction product mixture resulting from reactor 1.

The earlier German patent application No. 102005019373.0 of Apr. 26, 2005 (BASF AG) relates to a process for preparing ethylene amines in which ethylene oxide is reacted continuously with ammonia under water-free conditions over an inorganic ion exchanger in a first reaction step to give a reaction product comprising monoethanolamine diethanolamine and triethanolamine in a particular weight ratio and the reaction product is subsequently reacted continuously with ammonia in the presence of hydrogen and a hydrogenation catalyst in a second reaction step.

A parallel German patent application filed on the same date (BASF AG) relates to a process for preparing ethylene amines by reaction of ethylenediamine (EDA) in the presence of specific shaped heterogeneous catalyst bodies.

A parallel German patent application filed on the same date (BASF AG) relates to a process for preparing aminodiglycol (ADG) and morpholine by reacting diethylene glycol (DEG) with ammonia in the presence of specific shaped heterogeneous catalyst bodies.

BRIEF SUMMARY OF THE INVENTION

The present invention relates to a process for preparing ethylene amines by reaction of monoethanolamine (MEOA) with ammonia in the presence of a heterogeneous transition metal catalyst.

It was an object of the present invention to remedy the disadvantages of the prior art and discover an improved economical process for preparing ethylene amines, in particular ethylenediamine (EDA), diethylenetriamine (DETA), aminoethylethanolamine (AEEA), piperazine (PIP), triethylenetetramine (TETA) and/or higher linear polyethylene amines.

The process should give the acyclic amines such as ethylenediamine (EDA) and diethylenetriamine (DETA), in particular, in high yields, space-time yields and selectivities.

For example, the proportion of ethylenediamine and diethylenetriamine among the ethylene amines formed in the product mix should be increased compared to the prior art, e.g. greater than 70% by weight, and the proportion of piperazine (PIP) among the ethylene amines formed should be able to be limited according to requirements, e.g. to below 20% by weight, at a total yield of MEOA of, in particular, greater than 70%.

[Space-time yields are reported in "amount of product/ (catalyst volume·time)" ($kg/(l_{cat.} \cdot h)$) and/or "amount of product/(reactor volume·time)" ($kg/(l_{reactor} \cdot h)$)].

We have accordingly found a process for preparing ethylene amines by reacting monoethanolamine (MEOA) with ammonia in the presence of a heterogeneous transition metal catalyst, wherein the catalytically active composition of the catalyst before treatment with hydrogen comprises oxygen-comprising compounds of aluminum, copper, nickel and cobalt and the shaped catalyst body has a diameter of <3 mm in the case of a spherical shape or extrudate form, a height of <3 mm in the case of a pellet shape and in the case of all other geometries in each case an equivalent diameter $L = 1/a'$ of <0.70 mm, where a' is the external surface area per unit volume ($mm_s^2/mm_p^3$) with:

$$a' = \frac{A_p}{V_p},$$

where $A_p$ is the external surface area of the catalyst particle ($mm_s^2$) and $V_p$ is the volume of the catalyst particle ($mm_p^3$).

The surface area and the volume of the catalyst particle (the shaped catalyst body) are derived from the geometric dimensions of the particle (the shaped body) according to known mathematical formulae.

The volume can also be calculated by the following method, in which:
1. the internal porosity of the shaped body is determined (e.g. by measuring the water absorption in [ml/g of cat] at room temperature and a total pressure of 1 bar), 2. the displacement of the shaped body on immersion in a liquid is determined (e.g. by displacement of gas by means of a helium pycnometer) and
3. the sum of the two volumes is calculated.

The surface area can also be calculated theoretically by the following method, in which an envelope of the shaped body whose curve radii are not more than 5 μm (in order not to include the internal pore surface area by "intrusion" of the envelope into the pores) and which contacts the shaped body very intimately (no plane of section with the support) is defined. This would clearly correspond to a very thin film which is placed around the shaped body and a vacuum is then applied from the inside so that the film envelopes the shaped body very tightly.

DETAILED DESCRIPTION OF THE INVENTION

The monoethanolamine ($H_2N-CH_2-CH_2-OH$; MEOA) required as starting material can be prepared by known methods, for example by reaction of ethylene oxide (EO) with ammonia.

The reaction according to the invention is generally carried out at an absolute pressure in the range 1-250 bar, preferably 100-220 bar, in particular 150-200 bar, and generally at elevated temperature, e.g. in the temperature range 100-300° C., in particular 130-230° C., preferably 170-220° C.

MEOA and ammonia are preferably used in a molar ratio in the range $NH_3$:MEOA=1-15, particularly preferably in the range $NH_3$:MEOA=4-13, very particularly preferably in the range $NH_3$:MEOA=7-11.

In general, the catalysts used in the process of the invention are preferably used in the form of catalysts which either consist entirety of catalytically active composition and, if appropriate, a shaping aid (e.g. graphite or stearic acid) or are composed of the catalytically active components on a largely inactive support material.

The catalytically active composition can be introduced into the reaction vessel as powder or crushed material after milling or preferably be introduced into the reactor as shaped catalyst bodies, for example as pellets, spheres, rings, extrudates (e.g. rods, tubes) after milling, mixing with shaping aids, shaping and heat treatment.

The concentrations (in % by weight) indicated for the components of the catalyst are in each case, unless indicated otherwise, based on the catalytically active composition of the catalyst produced before treatment with hydrogen.

The catalytically active composition is defined as the sum of the masses of the catalytically active constituents and preferably comprises, before treatment with hydrogen, essentially the catalytically active constituents oxygen-comprising compounds of aluminum, copper, nickel and cobalt.

The sum of the abovementioned catalytically active constituents, calculated as $Al_2O_3$, CuO, NiO and CoO, in the catalytically active composition before treatment with hydrogen is, for example, from 70 to 100% by weight, preferably from 80 to 100% by weight, particularly preferably from 90 to 100% by weight, in particular from 95 to 100% by weight, very particularly preferably from >99 to 100% by weight.

The oxygen-comprising compounds of nickel, cobalt and copper, in each case calculated as NiO, CoO and CuO, are preferably comprised in the catalytically active composition (before treatment with hydrogen) in total amounts of from 10 to 80% by weight, particularly preferably from 15 to 60% by weight, very particularly preferably from 20 to 40% by weight, with the molar ratio of nickel to copper particularly preferably being greater than 1.

The catalytically active composition of the preferred catalysts in the process of the invention, comprises, before treatment with hydrogen, from 20 to 90% by weight, preferably from 40 to 85% by weight, particularly preferably from 60 to 80% by weight, of oxygen-comprising compounds of aluminum, calculated as $Al_2O_3$, from 1 to 30% by weight, preferably from 2 to 25% by weight, particularly preferably from 3 to 20% by weight, of oxygen-comprising compounds of copper, calculated as CuO, from 1 to 40% by weight, preferably from 3 to 30% by weight, particularly preferably from 5 to 20% by weight, of oxygen-comprising compounds of nickel, calculated as NiO, with the molar ratio of nickel to copper particularly preferably being greater than 1, more preferably greater than 1.2, particularly preferably from 1.8 to 8.5, and from 1 to 40% by weight, preferably from 3 to 30% by weight, particularly preferably from 5 to 20% by weight, of oxygen-comprising compounds of cobalt, calculated as CoO.

The catalysts having the composition mentioned can be produced by various methods. For example, they can be obtained by precipitation processes and preferably impregnation processes known to those skilled in the art.

Particularly preferred catalysts in the process of the invention are the catalysts which are disclosed in DE-A-19 53 263 (BASF AG) and comprise cobalt, nickel and copper and aluminum oxide and optionally silicon dioxide and have a metal content of from 5 to 80% by weight, in particular from 10 to 30% by weight, based on the total catalyst, with the catalysts comprising, calculated on the basis of the metal content, from 70 to 95% by weight of a mixture of cobalt and nickel and from 5 to 30% by weight of copper and the weight ratio of cobalt to nickel being from 4:1 to 1:4, in particular from 2:1 to 1:2, for example the catalyst used in the examples there which has the composition 10% by weight of CoO, 10% by weight of NiO and 4% by weight of CuO on $Al_2O_3$.

The catalyst used preferably has a bulk density in the range from 0.6 to 1.2 kg/l.

According to the invention, it has been noted that particularly high EDA and DETA selectivities are obtained when the catalyst is used in the form of small shaped bodies. For the purposes of the present invention, small shaped bodies are bodies whose diameter in the case of a spherical shape is in each case less than 3 mm, in particular less than 2.5 mm, e.g. in the range from 1 to 2 mm.

Correspondingly, small shaped bodies are also ones whose diameter in the case of extrudate form (extrudate length>>extrudate diameter) or whose height in the case of a pellet shape (pellet diameter>>pellet height) is in each case less than 3 mm, in particular less than 2.5 mm, e.g. in the range from 1 to 2 mm.

In the case of all other geometries, the shaped catalyst body used in the process of the invention in each case has an equivalent diameter L=1/a' of <0.70 mm, in particular <0.65 mm, e.g. in the range from 0.2 to 0.6 mm, where a' is the external surface area per unit volume ($mm_s^2/mm_p^3$), with:

$$a' = \frac{A_p}{V_p},$$

where $A_p$ is the external surface area of the catalyst particle ($mm_s^2$) and $V_p$ is the volume of the catalyst particle ($mm_p^3$).

(L=specific dimension of a shaped catalyst body).

In the process of the invention, the diffusion paths of the reactants and also of the products are shorter as a result of the small specific dimension of the catalyst particles. The mean residence time of the molecules in the pores and the probability of an undesirable subsequent reaction are consequently reduced. As a result of the defined residence time, an increased selectivity can therefore be achieved, especially in the direction of the desired EDA and DETA.

The catalyst is preferably present as a fixed bed in a reactor. The reactor is preferably a tube reactor or shell-and-tube reactor. The reaction of MEOA is preferably carried out in a single pass through the reactor.

The catalyst bed is preferably surrounded by an inert material both at the inlet of the reactor and the outlet of the reactor. As inert material, it is possible to use, for example, Pall rings, spheres of an inert material (e.g. ceramic, steatite, aluminum).

The reactor can be operated either in the upflow mode or the downflow mode. In the case of the preferred downflow mode, a liquid distributor for the reactor feed is preferably installed at the inlet of the reactor.

To maintain the catalyst activity, preference is given to feeding 0.01-1.00% by weight, particularly preferably 0.20-0.60% by weight, of hydrogen (based on the reactor feed MEOA+$NH_3$) into the reactor.

In the preferred continuous operation, selectivities (S) to EDA and DETA of preferably ≧60%, in particular 70-85%, are achieved at a conversion of 55-90% at an WHSV (weight hourly space velocity) of 0.25-1.25 kg/kg*h, preferably 0.4-1 kg/kg*h, (kg of MEOA per kg of cat. per hour), particularly preferably from 0.5 to 1.5 kg/kg*h.

Small amounts of piperazine ($S_{PIP}$ generally 5-25%), aminoethylethanolamine ($S_{AEEA}$ generally 3-13%) and higher amines ($S_{higher\ amines}$ generally 2-12%) are obtained as further products in the process of the invention.

In general, the crude reaction products from the process of the invention comprise only small amounts of cyclic amines as reaction products (in general in amounts of <20% by weight, in particular <15% by weight, very particularly preferably from 7 to 12% by weight).

In general, the crude reaction products from the process of the invention comprise only small amounts of tertiary amines as reaction by-products (in general in amounts of <10% by weight, in particular <7% by weight, very particularly preferably from 0 to 4% by weight).

The work-up of the product streams obtained in the process of the invention, which, in particular, comprise the particularly desired EDA and DETA but also N-(2-aminoethyl)-ethanolamine (AEEA), triethylenetetramine (TETA), piperazine (PIP), N-(2-aminoethyl)-piperazine (AE-PIP) and unreacted MEOA, can be carried out by distillation processes known to those skilled in the art. (cf., for example, PEP Report No. 138, "Alkyl Amines", SRI International, 03/1981, pages 81-99, 117, and DE-A-10349059 (BASF-AG)).

The distillation columns required for isolating the individual products, especially the particularly desired EDA and DETA, in pure form by distillation can be designed (e.g. number of theoretical plates, reflux ratio, etc.) by those skilled in the art using methods with which they would be familiar.

The fractionation of the reaction product mixture resulting from the reaction is, in particular, carried out by multistage distillation.

For example, the fractionation of the reaction product mixture resulting from the reaction is carried out by multistage distillation in two separation sequences, with ammonia and any hydrogen present being separated off first in the first separation sequence and fractionation into unreacted MEOA and EDA, PIP, DETA, AEEA, AE-PIP, TETA and higher ethylene amines being carried out in the second separation sequence.

The ammonia obtained from the reaction product mixture resulting from the reaction from the fractionation and/or MEOA obtained are/is preferably recirculated to the reaction.

EXAMPLES

The following catalysts were used for the reaction of MEOA with ammonia to form ethylene amines:

all catalysts were Cu/Co/Ni/gamma-$Al_2O_3$ catalysts as disclosed, for example, in DE-A-19 53 263 (BASF AG) and were produced by impregnation.

The catalysts 1-3 had the following composition before treatment (activation) with hydrogen:

10% by weight of CoO, 10% by weight of NiO and 4% by weight of CuO on gamma-$Al_2O_3$.

Catalyst 1 was in the form of extrudates (diameter D=4 mm).

Catalyst 2 was in the form of extrudates (diameter D=2.5 mm).

Catalyst 3 was obtained by appropriate impregnation of a gamma-$Al_2O_3$ extrudate having a diameter of 1.5 mm.

| Example | $D^{1)}$/mm | $L^{2)}$/mm |
|---|---|---|
| 1 (Comparison) | 4 | 6.5 |
| 2 | 2.5 | 6 |
| 3 | 1.5 | 6.9 |

[1)]mean extrudate diameter
[2)]mean extrudate length

Examples 1-3

| | D (extrudate) mm | Temperature °C. | Pressure bar | Space velocity kg/l · h | Conversion % | S(EDA + DETA) % |
|---|---|---|---|---|---|---|
| 1 (Comparison) | 4 | 174.8 | 202.7 | 0.54 | 64.0 | 71.9 |
| 2 | 2.5 | 175.0 | 220.0 | 0.55 | 65.0 | 76.0 |
| 3 | 1.5 | 175.0 | 200.0 | 0.55 | 66.0 | 80.5 |

It can be seen from the examples that increased conversions in the direction of EDA and DETA are achieved as the size of the shaped body decreases under otherwise identical test conditions.

The invention claimed is:

1. A process comprising: providing a starting material comprising monoethanolamine; and reacting the starting material with ammonia in the presence of a heterogeneous transition metal catalyst to form a reaction product comprising one or more ethylene amines; wherein the catalyst comprises a catalytically active composition, which prior to treatment with hydrogen, comprises a mixture of oxygen-containing compounds of aluminum, copper, nickel and cobalt; and wherein the catalyst is present as one or more shaped catalyst particles selected from spheres, extrudates, pellets and other geometries, wherein the sphere or extrudate has a diameter of <3 mm, the pellet has a height of <3 mm, and the other geometries have an equivalent diameter L=1/a' of <0.70 mm, where a' is the external surface area per unit volume ($mm_s^2/mm_p^3$) as defined by $$a' = \frac{A_p}{V_p}$$

where $A_p$ is the external surface area of the catalyst particle ($mm_s^2$) and $V_p$ is the volume of the catalyst particle ($mm_p^3$).

2. The process according to claim 1, wherein the one or more ethylene amines are selected from the group consisting of ethylenediamine (EDA), diethylenetriamine (DETA), aminoethylethanolamine (AEEA), piperazine (PIP), N-(2-aminoethyl)piperazine (AE-PIP), triethylenetetramine (TETA), and mixtures thereof.

3. The process according to claim 1, wherein the one or more ethylene amines comprises an acyclic ethylene amine.

4. The process according to claim 1, wherein the one or more ethylene amines are selected from the group consisting of ethylenediamine (FDA), diethylenetriamine (DETA), and mixtures thereof.

5. The process according to claim 1, wherein the sphere or extrudate has a diameter of <2.5 mm, the pellet has a height of <2.5 mm, and the other geometries have an equivalent diameter L=1/a' of <0.65 mm.

6. The process according to claim 1, wherein reacting the starting material is carried out in the further presence of hydrogen.

7. The process according to claim 1, wherein reacting the starting material is carried out at a temperature of 100 to 300° C.

8. The process according to claim 1, wherein reacting the starting material is carried out at an absolute pressure of 10 to 250 bar.

9. The process according to claim 1, wherein reacting the starting material is carried out in the gas phase, in the liquid phase, or in a supercritical phase.

10. The process according to claim 1, wherein the catalytically active composition, prior to treatment with hydrogen, comprises 20 to 90% by weight of one or more oxygen-containing compounds of aluminum, calculated as $Al_2O_3$, 1 to 30% by weight of one or more oxygen-containing compounds of copper, calculated as CuO, 1 to 40% by weight of one or more oxygen-containing compounds of nickel, calculated as NiO, and 1 to 40% by weight of one or more oxygen-containing compounds of cobalt, calculated as CoO.

11. The process according to claim 1, wherein the catalyst has a bulk density of 0.6 to 1.2 kg/l.

12. The process according to claim 1, wherein reacting the starting material is carried out in a reactor, and the catalyst is present in the reactor as a fixed bed.

13. The process according to claim 12, wherein the reactor is selected from the group consisting of tube reactors and shell-and-tube reactors.

14. The process according to claim 12, wherein reacting the starting material is carried out in a single pass through the reactor.

15. The process according to claim 12, wherein the reactor is operated in the upflow mode or in the downflow mode.

16. The process according to claim 1, wherein the monoethanolamine and the ammonia are reacted in a molar ratio of ammonia:monoethanolamine of 1 to 15.

17. The process according to claim 1, further comprising fractionating the reaction product in a multistage distillation.

18. The process according to claim 17, wherein the multistage distillation comprises a first separation sequence and a second separation sequence, wherein ammonia and hydrogen present in the reaction product are separated from a remainder of the reaction product in the first separation sequence, and wherein unreacted monoethanolamine, ethylenediamine (EDA), diethylenetriamine (DETA), aminoethylethanolamine (AEEA), piperazine (PIP), N-(2-aminoethyl)piperazine (AE-PIP), triethylenetetramine (TETA), and optionally other higher ethylene amines present in the remainder of the reaction product, are fractionated in the second separation sequence.

19. The process according to claim 18, wherein one or both of the ammonia obtained from the first separation sequence and the unreacted monoethanolamine obtained from the second separation sequence is recirculated to the reaction.

* * * * *